United States Patent
Weyand et al.

(10) Patent No.: US 7,371,216 B2
(45) Date of Patent: May 13, 2008

(54) METHOD FOR ASSESSING THE METABOLIC BASIS OF PHYSICAL FITNESS

(75) Inventors: Peter G. Weyand, Houston, TX (US); Matthew W. Bundle, Houston, TX (US)

(73) Assignee: William Marsh Rice University, Houston, TX (US)

( * ) Notice: Subject to any disclaimer, the term of this patent is extended or adjusted under 35 U.S.C. 154(b) by 492 days.

(21) Appl. No.: 11/030,674

(22) Filed: Jan. 6, 2005

(65) Prior Publication Data

US 2005/0245792 A1    Nov. 3, 2005

Related U.S. Application Data

(60) Provisional application No. 60/535,197, filed on Jan. 8, 2004.

(51) Int. Cl.
*A61B 5/00* (2006.01)
*A61B 5/103* (2006.01)

(52) U.S. Cl. ............ 600/300; 600/587; 600/595; 482/8; 482/9

(58) Field of Classification Search ............ 482/9
See application file for complete search history.

(56) References Cited

U.S. PATENT DOCUMENTS 4,281,663 A * 8/1981 Pringle ............ 600/502
5,410,472 A    4/1995 Anderson
6,736,759 B1 * 5/2004 Stubbs et al. ............ 482/8

OTHER PUBLICATIONS

Bundle et al., *High-speed Running Performance: A New Approach to Assesment and Prediction*, J. Appl. Physiol 95: 1955-1962 (2003).
Weyand et al., *Ambulatory Estimates of Maximal Aerobic Power From Foot—Ground Contact times and Heart Rates in Running Humans*, J. Appl. Physicol. 91: 451-458 (2001).
VO2 Max (10 pp.) [online] Retrieved from the Internet:<URL http://www.brianmac.demon.co.uk/vo2max.htm.

* cited by examiner

*Primary Examiner*—Robert L. Nasser, Jr.
*Assistant Examiner*—Patricia C Mallari
(74) *Attorney, Agent, or Firm*—Conley Rose, P.C.; Rodney B. Carroll

(57) ABSTRACT

The present invention includes a method for assessing the fitness of an individual. In one embodiment, the method comprises providing a physical fitness value of an individual by measuring a first trial of an activity conducted by the individual to provide a first measured component. The method further comprises measuring a second trial of an activity conducted by the individual to provide a second measured component. In addition, the method comprises determining the physical fitness values from the first and second measured components. In some embodiments, the method comprises estimating speed or mechanical power output values for the individual over a desired duration. In other embodiments, the method comprises determining the $VO_2$ max of the individual.

13 Claims, No Drawings

METHOD FOR ASSESSING THE METABOLIC BASIS OF PHYSICAL FITNESS

CROSS-REFERENCE TO RELATED APPLICATIONS

This non-provisional application claims the benefit of U.S. Provisional Application No. 60/535,197, filed Jan. 8, 2004, which is hereby incorporated by reference in its entirety.

STATEMENT REGARDING FEDERALLY SPONSORED RESEARCH OR DEVELOPMENT

This work was supported by the National Academy of Sciences through a federal government laboratory, United States Army Research Institute of Environmental Medicine.

BACKGROUND OF THE INVENTION

1. Field of the Invention

This invention relates to the field of physical fitness assessment and more particularly to the field of testing for physical fitness and predicting exercise performance capabilities.

2. Background of the Invention

The field of physical fitness assessment and testing has seen an increasing demand with rising public interest in physical fitness and the relevance of performance to soldiers, firefighters, athletes, and the like. For instance, with the high demand and financial stakes of professional and collegiate athletics, there is strong interest in accurately predicting and testing the physical fitness of the athletes. In addition, the increasingly health conscious public is interested in assessing their physical fitness.

Health clubs and physiological laboratories typically conduct elaborate fitness and performance assessments. Such assessments often test the aerobic and anaerobic fitness of participants. Several different tests have been used to make such aerobic and anaerobic assessments. For instance, tests to make an aerobic assessment typically determine the $VO_2$ max of a subject. This value may be measured by having an individual exercise (e.g., on a treadmill or a stationary bicycle) for a period of time ranging from five to thirty minutes. During such period of time, the passage of air in and out of the individual's nose is blocked, for example by a clip. A mouthpiece is placed in the individual's mouth and connected to equipment that measures the volume and composition of the air the person expires (e.g., a metabolic system, indirect calorimetry system, and the like), which is a device that determines the quantity of oxygen in the expired air. By comparing the quantity of oxygen in the expired air to the quantity of oxygen in the air taken in to the mouth, the quantity of oxygen used by the individual is determined, thereby providing the $VO_2$ max. The component of physical or aerobic fitness is measured by the quantity of oxygen taken from the air per a unit of time.

An example of an anaerobic test is the Wingate Test. With the Wingate test, a person typically pedals on a stationary bicycle at maximum effort for a set period of time with the power output of the bicycle measured. A sum of the bicycle's power output over the period of time is typically used as a comparison with such a sum from other people to determine the person's anaerobic fitness.

Drawbacks of the typical anaerobic and aerobic tests include the length of time and expense involved. For instance, aerobic tests typically require from 5 to 20 minutes of strenuous exercise. Further drawbacks include the use of sophisticated equipment. Additional drawbacks include, for instance, anaerobic fitness being limited to the power output of the stationary bicycle and not the power output of the individual being tested.

Consequently, there are needs for improved methods for assessing and predicting efforts that are determined by individual levels of anaerobic and aerobic fitness. Additional needs include less expensive and less complicated methods for assessing anaerobic and aerobic fitness.

BRIEF SUMMARY OF SOME OF THE PREFERRED EMBODIMENTS

These and other needs in the art are addressed in one embodiment by a method for assessing physical fitness of an individual. The method comprises measuring a first trial of an activity conducted by the individual to provide a first measured component. The method further comprises measuring a second trial of an activity conducted by the individual to provide a second measured component. In addition, the method comprises determining a physical fitness value from the first and second measured components, wherein the physical fitness value is suitable for assessing the physical fitness of the individual.

In another embodiment, needs in the art are addressed by a method for assessing physical fitness of an individual comprising measuring a first trial of an activity conducted by the individual at maximum intensity to provide a speed of the individual and measuring a second trial of an activity conducted by the individual at maximum intensity to provide a second speed of the individual. The method further comprises determining anaerobic reserve speed from the first and second speeds and determining a maximum speed supported by aerobic power of the individual. In addition, the method comprises determining a maximum speed supported by anaerobic power of the individual, and estimating a physical fitness value, wherein the physical fitness value comprises an estimated speed for a duration of the activity or another activity at maximum intensity.

In an additional embodiment, needs in the art are addressed by a method for assessing physical fitness of an individual comprising measuring a first trial of an activity conducted by the individual at maximum intensity to provide a first mechanical power output of the individual and measuring a second trial of an activity conducted by the individual at maximum intensity to provide a second mechanical power output of the individual. The method further comprises determining anaerobic reserve power from the first and second mechanical power outputs and determining a maximum mechanical power output supported by aerobic power of the individual. In addition, the method comprises determining a maximum mechanical power output supported by anaerobic power of the individual, and estimating a physical fitness value, wherein the physical fitness value comprises an estimated mechanical power output for a duration of the activity or another activity at maximum intensity.

Other embodiments include comparing an estimated physical fitness value to a set of values (e.g., estimated speed, $VO_2$ max, and the like). For instance, a $VO_2$ max of an individual can be compared to a $VO_2$ max of another individual. Additional embodiments include determining the $VO_2$ max of the individual. Further embodiments include determining such physical fitness values as an estimated maximum speed, a maximum speed supported by anaerobic and/or aerobic power, an estimated maximum mechanical power, a maximum mechanical power supported by anaerobic and/or aerobic power, $VO_2$ max, maximum anaerobic power and/or an estimated maximum anaerobic powers.

The methods for determining physical fitness values overcome problems in the art such as the time and expense involved with typical tests for assessing physical fitness. For instance, physical fitness can be assessed by the methods of the present invention more efficiently (e.g., quicker and less expensive) than the typical tests by applying algorithms using Equations and the measured results of two trials.

The disclosed devices and methods comprise a combination of features and advantages, which enable it to overcome the deficiencies of the prior art devices. The various characteristics described above, as well as other features, will be readily apparent to those skilled in the art upon reading the following detailed description.

DETAILED DESCRIPTION OF THE PREFERRED EMBODIMENTS

It has been discovered that physical performance capabilities of an individual can be accurately estimated over a range of exercise durations. It has been further discovered that from two measured trials (e.g., at maximum effort) the individual's anaerobic and aerobic fitness level can be quantified. Such performance capabilities and fitness levels can be used to assess the physical fitness of the individual. For instance, the performance capabilities and fitness level of the individual can be compared to those of others and/or to a standard value to assess the individual's fitness. Methods for predicting the physical performance capabilities and quantifying the fitness level use discovered Equations. The Equations include Equations (1)-(18) below. Without being limited by theory, it is believed that such methods allow the quantification of a biological relationship that relates exercise performance capabilities to the availability of metabolic power from different chemical energy sources in the body. It is further believed that Equations (1)-(18) below quantify such a biological relationship.

In an embodiment, the maximum speed an individual can maintain for a maximum intensity trial of any duration (e.g., the maximum speed by running, swimming, and the like) can be estimated by measuring or calculating the maximum speeds of the individual supported by the anaerobic and aerobic power of the individual. The maximum speed for any duration can be estimated by the following Equation (1):

$$Spd(t) = Spd_{aer} + (Spd_{an} - Spd_{aer}) * e^{(-ks*t)} \quad (1).$$

In Equation (1), t is the duration of a maximum intensity activity by the individual, Spd(t) is the estimated speed for a maximum intensity activity at duration t, $Spd_{an}$ is the maximum speed supported by anaerobic power of the individual (e.g., maximum speed at 3 seconds or less), and $Spd_{aer}$ is the maximum speed supported by the aerobic power of the individual (maximum speed maintained at $VO_2$ max). The reference e is the base of the natural logarithm. The constant ks is the decrements in speed that occur with increments in activity duration. It is to be understood that the value of ks can vary depending on the type of activity. Without being limited by theory, it is believed that ks allows the Equations to take into account that a typical individual conducting a maximum intensity activity may have a decrease in speed over increasing durations of time. Without further being limited by theory, it is believed that ks will not substantially vary between individual humans. In some embodiments, ks can be determined from empirical data. For instance, a value for ks can be determined from data such as a series of all-out trials as well as measurements of individual aerobic and anaerobic maximums that have been collected from any desired amount of subjects for the desired exercise. In an embodiment, a value for ks can be from about 0.005 to about 0.05, alternatively from about 0.005 to about 0.03, and alternatively from about 0.010 to about 0.020. In an embodiment, ks may be about 0.040 for swimming activities. In other embodiments, ks can be selected from among 0.013, 0.0123, 0.0134, and 0.0136. In some embodiments, the value for ks is 0.013. Further embodiments include selecting a ks value of 0.013 for general activities or non-specialized individuals, selecting a ks value of 0.0123 for sprinting specialists, selecting a ks value of 0.0134 for middle distance specialists, and selecting a ks value of 0.0136 for long distance specialists. General activities refer to non-athletic activities. Without being limited by theory, general activities include typical walking, yard work, house work, any vigorous physical exercise, and the like. Non-specialized individuals refer to individuals that are not athletes, not training to be athletes, or not conditioning their body for an athletic activity. Sprinting specialists include individuals conditioned to perform maximum intensity activities of durations from about 1 second to about 50 seconds. Middle distance specialists include individuals conditioned to perform maximum intensity activities of durations from about 50 seconds to about 300 seconds. Long distance specialists include individuals conditioned to perform maximum intensity activities for durations longer than about 300 seconds. Without being limited by theory, the maximum intensity activity includes running, swimming, skiing, skating, and the like. In an embodiment, the maximum intensity activity is running. Maximum intensity refers to the individual conducting an activity at about 100% effort for a period of time.

It is to be understood that Equation (1) can be mathematically altered to also provide a prediction of a duration, a speed, or a distance for a maximum intensity activity by the individual. For instance, for a desired Spd(t), Equation (1) can be rearranged to provide for a determination of t.

$Spd_{an}$ and $Spd_{aer}$ can be measured for an individual or calculated from the following Equations (2) and (3):

$$Spd_{aer} = Spd_1 - Spd_{an\,res} * e^{(-ks*t_1)} \quad (2)$$

$$Spd_{an} = Spd_{an\,res} + Spd_{aer} \quad (3).$$

It is to be understood that $Spd_{an}$ and $Spd_{aer}$ can be measured by any conventional means. For instance, $Spd_{an}$ can be measured as the maximum speed the individual attains in a trial conducted at maximum intensity for a duration (e.g., a duration of 3 seconds or less), and $Spd_{aer}$ can be measured as the maximum speed the individual attains in a trial at the $VO_2$ max of the individual.

$Spd_{an\,res}$ represents the anaerobic reserve speed and is determined from the following Equation (4):

$$Spd_{an\,res} = (Spd_1 - Spd_2)/[e^{(-ks*t_1)} - e^{(-ks*t_2)}] \quad (4).$$

The anaerobic reserve speed refers to the maximum speed that can be supported for a maximum intensity effort of a period of time (for example, from about 2 to about 3 seconds) minus the maximum speed that can be supported by the individual's maximum aerobic power (i.e., $VO_2$ max).

In an embodiment, $Spd_{aer}$, $Spd_{an}$, and $Spd_{an\,res}$ are determined by measuring in two trials the time that it takes the individual to travel a set distance at maximum intensity. The two trials are conducted over different distances. The individual can be covering the timed distance by running, swimming, skiing, skating, and the like. In an embodiment, the individual covers the distance by running. The individual can cover the distance in any environment suitable for the activity. For instance, in an embodiment in which the individual is covering the distance by running, the individual can run on a track or a fixed running device such as a treadmill. The individual can be timed by stopwatch, speed gun, or any other suitable device or method. In an alternative embodiment, an accelerometer is used to measure $t_1$ and $t_2$ and/or $Spd_1$ and $Spd_2$. Accelerometers are speed and time measurement devices that are typically mounted in the shoes of the individual. Without limitation, a commercial example of an accelerometer is FS1 available from FitSense Technology Inc.

In the first trial, the time that it takes the individual to cover a set distance is measured with the individual running at maximum intensity over the set distance. In an embodiment, the second trial is not conducted until the individual completes a resting period. The resting period can include waiting to conduct the second trial until after the individual has a heart rate at about 120 or less, alternatively waiting until the individual is able to perform a second maximum intensity effort (e.g., at 100% effort). The second trial is conducted over a set distance. The time that it takes the individual to cover the second set distance is also measured with the individual running at maximum intensity over the second set distance.

The terms $t_1$ and $t_2$ are the measured times that comprise the duration of the individual to cover the set distances for the first and second trials, respectively. $Spd_1$ and $Spd_2$ are the speeds of the individual at maximum intensity for the first and second trials, respectively, over the set distances. It is to be understood that speed can be determined from the known distance and measured time. It is to be further understood that $t_1$ and $t_2$ are different durations. In an embodiment, $t_1$ and $t_2$ are of any desired and different durations. In another embodiment, $t_1$ and $t_2$ are between about 1 second and about 3 hours, alternatively between about 3 seconds and about 3 hours, further alternatively between about 3 seconds and about 300 seconds, and further alternatively between about 5 seconds and about 200 seconds.

The metabolic power supporting the maximum intensity in an activity may be estimated according to the following Equation (5):

$$E(t) = Spd(t)*PS \quad (5).$$

E(t) represents the metabolic power supporting the maximum intensity in an activity, which represents the individual's metabolic rate or metabolic power during a maximum intensity effort for a period of time (e.g., from about 2 to about 3 seconds). P is a power constant that can vary by the individual and/or activity. PS represents a constant value for the energy cost of the exercise. For instance, it represents the amount of oxygen or kcals burned per unit mass and distance (e.g., kcals per kilogram of body weight per mile run or kcals per unit mechanical work performed on a cycle). In an embodiment, PS is directly measured. For instance, it may be directly measured by collecting a person's expired gases while they exercise at a steady intensity for a period of at least five minutes. As an example, in an embodiment wherein the activity is running, PS is obtained by dividing a volume rate of oxygen uptake by the speed of the run, which provides energy expended by the runner per unit distance. In other embodiments, PS is from about 172 ml $O_2$/(kg*km) to about 228 ml $O_2$/(kg*km), alternatively about 200 ml $O_2$/(kg*km).

In some embodiments, the maximum aerobic power ($E_{aer\ max}$) and maximum anaerobic power ($E_{an\ max}$) can be determined from the following Equations (6) and (7):

$$E_{aer\ max} = Spd_{aer}*PS \quad (6)$$

$$E_{an\ max} = Spd_{an}*PS \quad (7).$$

$E_{aer\ max}$ represents the $VO_2$ max for the individual. $VO_2$ max refers to the maximum amount of oxygen the individual can use in one minute per kilogram of body weight. $E_{an\ max}$ refers to the maximum rate at which chemical energy may be liberated within or by substantially all of the muscles involved in the maximum intensity activity. It is to be understood that PS is the power constant.

In other embodiments, the maximum aerobic power and maximum anaerobic power may be estimated for any duration at maximum intensity. An estimated maximum aerobic power ($E_{aer}(t)$) can be determined for a desired t by the following Equation (8):

$$E_{aer}(t) = E_{aer\ max}(1 - e^{kar*t}) \quad (8).$$

The constant kar describes the increments in aerobic power that occur with increments in activity duration. It is to be understood that the value of kar can vary depending on the type of activity. Without being limited by theory, it is believed that kar allows Equation (8) to take into account that a typical individual conducting a maximum intensity activity may have an increase in aerobic power over increasing durations of time. Without further being limited by theory, it is believed that kar will not substantially vary between individual humans. In some embodiments, kar can be determined from empirical data. For instance, a value for kar can be determined from measurements of aerobic power during a series of all-out trials (e.g., at maximum intensity) from any desired amount of subjects for the desired exercise. In an embodiment, a value for kar can be from about 0.03 to about 0.07, and alternatively from about 0.02 to about 0.4.

An estimated maximum anaerobic power ($E_{an}(t)$) can be determined for a desired t by the following Equation (9):

$$E_{an}(t) = (E_{an\ max})*e^{-kan*t} \quad (9).$$

The constant kan describes the decrements in anaerobic power that occur with increments in activity duration. It is to be understood that the value of kan can vary depending on the type of activity. Without being limited by theory, it is believed that kan allows Equation (9) to take into account that a typical individual conducting a maximum intensity activity may have a decrease in anaerobic power over increasing durations of time. Without further being limited by theory, it is believed that kan will not substantially vary between individual humans. In some embodiments, kan can be determined from empirical data. For instance, a value for kan can be determined from measurements of anaerobic power during a series of all-out trials (e.g., at maximum intensity) from any desired amount of subjects for the desired exercise. In an embodiment, a value for kan can be from about 0.02 to about 0.04, and alternatively from about 0.02 to about 0.05.

In other embodiments, the mechanical power output of the individual is measured in two trials and used to predict the performance capabilities and quantify the fitness levels of the individual. The mechanical power output of the individual can be measured from the individual operating any suitable device wherein the mechanical power output and time can be measured. Mechanical power output refers to the exerted force in relation to the distance through which the force acts. Without limitation, examples of such devices include a mobile or stationary bicycle, a swimming flume, a rowing machine, an elliptical machine, a stair stepper, and any other suitable device. In an embodiment, the device is a stationary bicycle. In another embodiment, the device is a mobile cycle ergometer. In some embodiments, the device (e.g., bicycle) includes a measurement apparatus that is capable of measuring the mechanical power output and time. Without limitation, examples of suitable measurement apparatuses include a strain gauge, piezoelectric devices, piezoresistive capacitive devices, and the like. An ergometer is a non-limiting example of a strain gauge. A commercial example of an ergometer is a straomn-gage based technology that is commercially available as the SRM ERGOMETER from SRM Inc. of Germany.

For such other embodiments, it is to be understood that the mechanical power output replaces the speed components from the embodiments of Equations (1)-(9). Therefore, Equations (10)-(18) noted below correlate to Equations (1)-(9) by replacing the speed components with mechanical power output components. For instance, the speed components of Equation (1) are replaced with mechanical power output components to provide Equation (10) as follows:

$$PO(t)=PO_{aer}+(PO_{an}-P_{aer})*e^{(-kP*t)} \qquad (10).$$

In Equation (10), PO(t) is the estimated mechanical power output of a maximum intensity by the individual, $PO_{aer}$ is the maximum mechanical power output supported by the aerobic power of the individual (maximum mechanical power output maintained at $VO_2$ max), and $PO_{an}$ is the maximum mechanical power output supported by the anaerobic power of the individual. In addition, t is the duration of a maximum intensity activity by the individual. The constant kP is the decrements in power that occur with increments in activity duration. It is to be understood that the kP constant for Equations (10)-(18) is different than the ks constant for Equations (1)-(9). Without being limited by theory, it is believed that the constant kP will not substantially vary between individual humans. Without further being limited by theory, kP can be determined from empirical data. A value for kP can be determined from data such as a series of all-out trials as well as measurements of individual aerobic and anaerobic maximums that have been collected from any desired amount of subjects for the desired exercise. In an embodiment, a value of kP can be from about 0.01 to about 0.06, alternatively from about 0.02 to about 0.03, and alternatively about 0.026.

$PO_{aer}$ and $PO_{an}$ can be measured for an individual or calculated from the following Equations (11) and (12):

$$PO_{aer}=PO_1-PO_{an\ res}*e^{(-kP*t_1)} \qquad (11)$$

$$PO_{an}=PO_{an\ res}+PO_{aer} \qquad (12).$$

It is to be understood that $PO_{aer}$ and $PO_{an}$ can be measured by any conventional means. For instance, $PO_{an}$ can be measured as the maximum mechanical power output the individual attains in a trial conducted at maximum intensity for a duration (e.g., a duration of 3 seconds or less), and $PO_{aer}$ can be measured as the maximum mechanical power output the individual attains in a trial at the $VO_2$ max of the individual.

$PO_{an\ res}$ represents the anaerobic reserve power and is determined from the following Equation (13):

$$PO_{an\ res}=(PO_1-PO_2)/[e^{(-kP*t_1)}-e^{(-kP*t_2)}] \qquad (13).$$

The anaerobic reserve power ($PO_{an\ res}$) refers to the maximum power that may be supported at maximum intensity for a period of time (e.g., from about 2 to about 3 seconds) minus the maximum power that can be supported by the individual's maximum aerobic power (e.g., $VO_2$ max). It is to be understood that Equations (11)-(13) correlate to Equations (2-4). The terms $t_1$ and $t_2$ are the measured times that comprise the duration of the individual to attain the maximum intensity for the first and second trials, respectively. $PO_1$ and $PO_2$ are the maximum mechanical power output for the first and second trials, respectively. It is to be understood that $t_1$ and $t_2$ are different durations. In an embodiment, $t_1$ and $t_2$ are of any desired and different durations. In another embodiment, $t_1$ and $t_2$ are between about 1 second and about 3 hours, alternatively between about 3 seconds and about 3 hours, further alternatively between about 3 seconds and about 300 seconds, and further alternatively between about 5 seconds and about 200 seconds.

In an embodiment, two trials at maximum intensity are conducted on the device, for instance a stationary or mobile bicycle. The individual operates the device at maximum intensity in the two trials at desired durations. The two trials are conducted at different durations (t). The measurement apparatus (e.g., strain gauge) measures and records the highest mechanical power output attained for each trial. From each trial, the measurement apparatus measures the mechanical power output ($PO_1$ and $PO_2$) for durations $t_1$ and $t_2$. $PO_{aer}$, $PO_{an}$, and $PO_{an\ res}$ can then be determined from Equations (11), (12), and (13). From such determinations, PO(t) can be estimated for any given duration by using Equation (10).

The metabolic power supporting the maximum intensity in an activity may be estimated according to the following Equation (14):

$$E(t)=PO(t)*PC \qquad (14).$$

E(t) represents the metabolic power supporting the maximum intensity in an activity. PC is a power constant and relates each unit of mechanical power provided to the metabolic power expended. PC further represents the body's rate of liberation of chemical energy (e.g., metabolic rate) to perform at a given mechanical power output. In an embodiment, PC may be determined by dividing mechanical power by metabolic power, which is the inverse of efficiency. The power constant PC may be from about 3.8 to about 5.2, alternatively about 4.5.

In some embodiments, the maximum aerobic power ($E_{aer\ max}$) and maximum anaerobic power ($E_{an\ max}$) can be determined from the following Equations (15) and (16):

$$E_{aer\ max}=PO_{aer}*PC \qquad (15)$$

$$E_{an\ max}=PO_{an}*PC \qquad (16).$$

As with Equations (6) and (7), $E_{aer\ max}$ represents the $VO_2$ max for the individual, and $E_{an\ max}$ represents $_{max}$ the maximum rate at which chemical energy may be liberated anaerobically within all of the muscles involved in the maximum intensity activity.

In an embodiment, by using the determined $E_{aer\ max}$ and $E_{an\ max}$, $E_{aer}(t)$ and $E_{an}(t)$ can be estimated for a desired duration t by the following Equations (17) and (18):

$$E_{aer}(t)=E_{aer\ max}(1-e^{kar*t}) \qquad (17).$$

$$E_{an}(t)=(E_{an\ max})*e^{-kan*t} \qquad (18)$$

In an embodiment, the physical fitness of two or more individuals can be compared to each other when one of the individuals has speed measured in two trials (e.g., measuring Spd$_1$ and Spd$_2$ while running) and another individual has mechanical power output measured in two trials (e.g., measuring PO$_1$ and PO$_2$ while operating a bicycle). A method for comparing their physical fitness includes predicting maximum speed of an individual at various durations and predicting maximum mechanical power output of an individual at various durations. The individuals can be the same or different individuals. It is to be understood that the methods are not limited to one or two individuals but instead can include more than two individuals. It is to be understood that predicting the maximum speed includes determining Spd$_{an}$, Spd$_{aer}$, and Spd$_{an\ res}$ by Equations (2)-(4) and using Equation (1) to predict the maximum speed at various durations. It is to be further understood that predicting the maximum mechanical power output includes determining PO$_{an}$, PO$_{aer}$, and PO$_{an\ res}$ by Equations (11)-(13) and using Equation (10) to predict the maximum mechanical power outputs at various durations. The method further includes reducing the estimated speeds by the determined value of Spd$_{aer}$ and reducing the estimated maximum mechanical power outputs by the determined value of PO$_{aer}$. Without being limited by theory, reducing the estimated speeds by Spd$_{aer}$ will zero out the speed aspect of a plotted curve of the estimated speed wherein the plot has the estimated speeds (e.g., Spd(t)) as one axis and duration (e.g., t) as the other axis. Without further being limited by theory, reducing the estimated mechanical power outputs by PO$_{aer}$ will zero out the power aspect of a plotted curve of the estimated mechanical power outputs wherein the plot has the estimated power outputs (e.g., PO(t)) as one axis and duration (e.g., t) as the other axis. It is believed that subtracting Spd$_{aer}$ and PO$_{aer}$ will zero out the respective axes because the lowest estimated points on their respective plots may correspond to Spd$_{aer}$ and PO$_{aer}$. In alternative embodiments, the estimated speeds and estimated mechanical power outputs are not reduced.

The method further includes providing relative anaerobic reserve for the estimated speeds and estimated mechanical power outputs. Providing the relative anaerobic reserve includes dividing the estimated speeds (with Spd$_{aer}$ subtracted therefrom) by Spd$_{an\ res}$ and includes dividing the estimated mechanical power outputs (with PO$_{aer}$ subtracted therefrom) by PO$_{an\ res}$. The method further includes applying an appropriate duty factor to the relative anaerobic reserve values. Without being limited by theory, the duty factor represents the ratio of muscle activation time to total time (e.g., of a stride or pedal rotation). The duty factor to be applied to the relative anaerobic reserve values for speed are from about 0.4 to about 0.9, alternatively from about 0.4 to about 0.75, and alternatively from about 0.4 to about 0.6, and further alternatively about 0.5. The duty factor to be applied to the relative anaerobic reserve values for power are from about 0.15 to about 0.90, alternatively from about 0.15 to about 0.75, and alternatively from about 0.15 to about 0.6, and further alternatively about 0.25. Applying the duty factor includes multiplying the appropriate duty factor to the relative anaerobic reserve values. Applying the anaerobic reserve values allows physical fitness of individuals to be directly compared to each other regardless of the activity at which the individuals conducted their trials.

The methods and algorithms using the above-identified embodiments (e.g., Equations) may be written into any suitable software. For instance, algorithms using the Equations can be written into software to provide the estimated and determined values. Such predictions and determined values can be stored electronically (e.g., in a database) and compared to past estimated and determined values for the individual or to such values of other individuals.

It is to be understood that the present invention is not limited to the above-identified embodiments but can also include fitness equipment comprising such embodiments. For instance, fitness equipment such as bicycles, treadmills, and the like can have equipment that include the above-disclosed equations and embodiments for assessing and determining the individual's physical fitness during or after using such equipment. Without limitation, the fitness equipment can incorporate the above-identified Equations and embodiments. As an example, the individual can conduct two trials on a treadmill with the treadmill recording t for each trial. Equipment on and/or connected to the treadmill determines values such as Spd$_{an}$, Spd$_{aer}$, Spd(t), E$_{aer}$(t), E$_{an}$(t), and the like. Software remote to the equipment or incorporated into the equipment can be used to make such determinations.

It is to be understood that the present invention is not limited to Equations (1)-(18) but instead also includes variations to such Equations. For instance, Equation (1) can be varied to the following:

$$Spd(t) = Spd_{aer} + (Spd_{an\ res}) * e^{(-kS*t)}$$

which provides the same result as Equation (1). Such variation is a result of varying Equation (3).

The individual can be a human. However, it is to be understood that the individual is not limited to humans but instead can also include horses, dogs, and the like.

The above discussion is meant to be illustrative of the principles and various embodiments of the present invention. Numerous variations and modifications will become apparent to those skilled in the art once the above disclosure is fully appreciated.

The invention claimed is:

1. A method for assessing physical fitness of an individual, comprising:
   (A) measuring a component during a first trial of an activity conducted by the individual to provide a first measured component;
   (B) measuring a component during a second trial of an activity conducted by the individual to provide a second measured component; and
   (C) determining a physical fitness value from the first and second measured components, wherein the physical fitness value is suitable for assessing the physical fitness of the individual, wherein determining the physical fitness value further comprises determining an anaerobic reserve speed of the individual from the first and second measured components.

2. The method of claim 1, further comprising determining a maximum speed supported by aerobic power of the individual.

3. The method of claim 2, further comprising determining a maximum speed supported by anaerobic power of the individual.

4. A method for assessing physical fitness of an individual, comprising;
   (A) measuring a component during a first trial of an activity conducted by the individual to provide a first measured component;
   (B) measuring a component during a second trial of an activity conducted by the individual to provide a second measured component;
   (C) determining a physical fitness value from the first and second measured components, wherein the physical fitness value is suitable for assessing the physical fitness of the individual; and (D) comparing the estimated physical fitness value to a set of values and providing a relative anaerobic reserve value for the estimated physical fitness value.

5. The method of claim 4, further comprising applying a duty factor to the relative anaerobic reserve value.

6. A method for assessing physical fitness of an individual, comprising:
- (A) measuring a component during a first trial of an activity conducted by the individual at maximum intensity to provide a first speed of the individual;
- (B) measuring a component during a second trial of an activity conducted by the individual at maximum intensity to provide a second speed of the individual;
- (C) determining anaerobic reserve speed from the first and second speeds;
- (D) determining a maximum speed supported by aerobic power of the individual;
- (E) determining a maximum speed supported by anaerobic power of the individual; and
- (F) estimating a physical fitness value, wherein the physical fitness value comprises an estimated speed for a duration of the activity or another activity at maximum intensity.

7. The method of claim 6, further comprising determining a value for $VO_2$ max of the individual, a maximum anaerobic power of the individual, or combinations thereof.

8. A method for assessing physical fitness of an individual, comprising:
- (A) measuring a component during a first trial of an activity conducted by the individual to provide a first measured component, wherein the first measured component comprises duration of the first trial;
- (B) measuring a component during a second trial of an activity conducted by the individual to provide a second measured component, wherein the second measured component comprises duration of the second trial; and
- (C) determining a physical fitness value from the first and second measured components, wherein the physical fitness value is suitable for assessing the physical fitness of the individual.

9. The method of claim 8, wherein the first and second trials are conducted at maximum intensity.

10. The method of claim 8, wherein determining the physical fitness value further comprises determining a $VO_2$ max of the individual.

11. An exercise device suitable for assessing physical fitness of an individual, wherein the exercise device comprises a measurement device, said measurement device having software which assesses the physical fitness of the individual using the method of claim 8.

12. The method of claim 8, wherein determining the physical fitness value further comprises estimating a physical fitness value for a duration of the activity.

13. The method of claim 8, further comprising
- (D) comparing the estimated physical fitness value to a set of values.

* * * * *